(12) United States Patent
Maunsell et al.

(10) Patent No.: US 11,096,886 B2
(45) Date of Patent: Aug. 24, 2021

(54) OAT LIPID EXTRACT

(71) Applicants: Oat Services Ltd, Southampton (GB); Swedish Oat Fiber, Bua (SE)

(72) Inventors: Cark Maunsell, Southampton (GB); Christopher Smith, Nottingham (GB)

(73) Assignees: Oat Services Ltd, Southampton (GB); Swedish Oat Fiber, Bua (SE)

( * ) Notice: Subject to any disclaimer, the term of this patent is extended or adjusted under 35 U.S.C. 154(b) by 0 days.

(21) Appl. No.: 16/490,114

(22) PCT Filed: Feb. 28, 2018

(86) PCT No.: PCT/GB2018/050521
§ 371 (c)(1),
(2) Date: Aug. 30, 2019

(87) PCT Pub. No.: WO2018/158572
PCT Pub. Date: Sep. 7, 2018

(65) Prior Publication Data
US 2020/0069569 A1    Mar. 5, 2020

(30) Foreign Application Priority Data

Mar. 1, 2017 (GB) ..................................... 1703321
Aug. 18, 2017 (GB) ..................................... 1713276

(51) Int. Cl.
| | | |
|---|---|---|
| *A61K 8/9794* | (2017.01) | |
| *A61K 8/55* | (2006.01) | |
| *A61K 8/60* | (2006.01) | |
| *A61K 36/899* | (2006.01) | |
| *A61Q 1/02* | (2006.01) | |
| *A61Q 1/06* | (2006.01) | |
| *A61Q 1/12* | (2006.01) | |
| *A61Q 5/02* | (2006.01) | |
| *A61Q 5/12* | (2006.01) | |
| *A61Q 17/04* | (2006.01) | |
| *A61Q 19/00* | (2006.01) | |
| *A61Q 19/08* | (2006.01) | |

(52) U.S. Cl.
CPC ............ *A61K 8/9794* (2017.08); *A61K 8/553* (2013.01); *A61K 8/602* (2013.01); *A61K 36/899* (2013.01); *A61Q 1/02* (2013.01); *A61Q 1/06* (2013.01); *A61Q 1/12* (2013.01); *A61Q 5/02* (2013.01); *A61Q 5/12* (2013.01); *A61Q 17/04* (2013.01); *A61Q 19/007* (2013.01); *A61Q 19/08* (2013.01); *A61K 2236/333* (2013.01)

(58) Field of Classification Search
None
See application file for complete search history.

(56) References Cited

U.S. PATENT DOCUMENTS

| | | |
|---|---|---|
| 5,026,548 A | 6/1991 | Evans et al. |
| 5,169,660 A | 12/1992 | Collins et al. |
| 5,466,782 A | 11/1995 | Rousset |
| 5,620,692 A * | 4/1997 | Potter ................... A61Q 17/04 424/401 |
| 6,495,140 B1 | 12/2002 | Collins et al. |
| 2010/0092651 A1 | 4/2010 | Kaukovirta-Norja et al. |
| 2014/0066510 A1 | 3/2014 | Redmond et al. |

FOREIGN PATENT DOCUMENTS

| | | |
|---|---|---|
| WO | 9711141 A1 | 3/1997 |
| WO | 9965459 A1 | 12/1999 |
| WO | 2008096044 A1 | 8/2008 |
| WO | 2010104444 A1 | 9/2010 |

OTHER PUBLICATIONS

Oat Cosmetics, "Oat Lipid", https://oatcosmetics.com/oat/oat-lipid/, accessed Feb. 13, 2021 (Year: 2015).*
Oat Cosmetics, "Oat Lipid", https://web.archive.org/web/20160126214947/https://oatcosmetics.com/oat/oat-lipid/, Jan. 26, 2016 (Year: 2016).*
Zhou Meixue et al: "Oat Lipids", Journal of the American Oil Chemists' Society (JAOCS), Springer, DE, vol. 76, No. 2, Feb. 1, 1999 (Feb. 1, 1999), pp. 159-169, XP001537711, ISSN: 0003-021X, DOI: 10.1007/S11746-999-0213-1 figure 1; table 3.
Foresell P et al: "Comparision of methods for separating polar lipids from oat oil", Fett—Lipid. Fat Science Technology, Wiley-VCH Verlag, Weinheim, DE, vol. 94, No. 9, Jan. 1, 1992 (Jan. 1, 1992), pp. 355-358, XP003027000, ISSN: 0931-5985, DOI: 10.1002/LIPI.19920940909 table 4.
Robert A. Moreau et al: "Pressurized Liquid Extraction of Polar and Nonpolar Lipids in Corn and Oats with Hexane, Methylene Chloride, Isopropanol, and Ethanol", Journal of the American Oil Chemists' Society, vol. 80, No. 11, Nov. 1, 2003 (Nov. 1, 2003), pp. 1063-1067, XP055473091, figure 4.
Mika Kaimainen et al: "Polar lipid fraction from oat: characterization and use as an o/w emulsifier", European Food Research and Technology; Zeitschrift Fur Lebensmitteluntersuchung Und—Forschung A, Springer, Berlin, DE, vol. 235, No. 3, Jul. 18, 2012 (Jul. 18, 2012), pp. 507-515, XP035098768, ISSN: 1438-2385, DOI: 10.1007/S00217-012-1780-1 abstract.

* cited by examiner

*Primary Examiner* — Melissa L Fisher
(74) *Attorney, Agent, or Firm* — Young Basile Hanlon & MacFarlane, P.C.

(57) ABSTRACT

A substantially solvent-free oat lipid extract containing neutral and polar lipid fractions, a method of manufacturing a substantially solvent-free oat lipid extract and compositions containing it.

20 Claims, No Drawings

OAT LIPID EXTRACT

CROSS REFERENCE TO RELATED APPLICATION(S)

The present application claims priority to and the benefit of United Kingdom Patent Application No. GB 1703321.8, filed Mar. 1, 2017, and United Kingdom Patent Application No. GB 1713276.2, filed Aug. 18, 2017, the entire disclosures of which are hereby incorporated by reference.

TECHNICAL FIELD

This invention relates to an oat lipid extract. In particular, this invention relates to an oat lipid extract which is high in polar lipids and is substantially free from solvent, and to compositions containing the extract.

BACKGROUND

Oats (*Avena sativa*) are cultivated worldwide and form an important dietary staple for people in a number of countries. They are a rich source of protein, and contain a number of important minerals and lipids, as well as β-glucan, a mixed-linkage polysaccharide which forms an important part of oat dietary fibre.

Oatmeal has been known for centuries to have dermatological benefits, and has traditionally been used as a soothing agent to relieve itching and irritation associated with a range of xerotic dermatoses. In 1945 a colloidal oatmeal, produced by finely grinding the oat and boiling it to extract the colloidal material, first became available. Colloidal oatmeal is used to relieve dry skin patches, psoriasis, acne, insect bites and other itching rashes, and may simply be dispersed in bath water where it forms a dispersion which coats the skin, moisturising and protecting it.

Today, colloidal oatmeal is formulated into a wide variety of dosage forms from powders for the bath to shampoos, shaving gels and moisturising cream. Colloidal oatmeal is gentle on the skin and can be used on young babies and children, as well as on those with sensitive skin. At least some of the soothing properties of colloidal oatmeal may be attributable to avenanthramides, the main polyphenolic antioxidants in oats, which have been shown to reduce inflammation and pruritogen-induced scratching in murine models (Fowler, J. F. J. Drugs Dermatol. 2014 October; 13(10): 1180-3). Other compounds present within oats include flavonoids, flavonolignans, triterpenoid saponins, sterols and tocopherols.

Oat oil, extracted from the oat kernel, is now commercially available and used in cosmetic products, typically for use on the skin and/or hair. Oat oil provides many of the same benefits as colloidal oatmeal, while delivering a greater concentration of important omega fatty acids and antioxidants, and being more suited to incorporation into cosmetic and pharmaceutical products.

Oat oil is principally composed of triglycerides, with small amounts of di and mono-glycerides and free fatty acids. Of particular interest in skincare applications are the polar lipids, which include ceramides and phospholipids. Typically, oat oil contains up to 10% of polar lipids, more usually 3-4%, of which only a small proportion are ceramides. For example, Oat Lipid e, produced by Oat Services Limited, has the following composition:

| | |
|---|---|
| Neutral lipids | 90.0% |
| Triacylglycerols | 59.5% |
| Cholesterols/sterols | 11.8% |
| Other neutral lipids | 18.7% |

*-continued*

| | |
|---|---|
| Polar lipids | 10.0% |
| monogalactosyldiacylglycerol/digalactosyldiacylglycerol | 3.1% |
| Ceramides | 1.2% |
| Phosphatidylcholine | 1.0% |
| Phosphatidylethanolamine | 1.7% |
| Other polar lipids | 4.0% |

Ceramides are a type of sphingolipid which are naturally occurring in plant and animal products, and have been used in cosmetics since the late $19^{th}$ Century. Six classes of ceramide are naturally found in the epidermis, creating a barrier which reduces infection and retains moisture. These ceramides are substantially equivalent to phyto-derived ceramides, which, when applied topically, integrate into the skin barrier layers and are very resistant against exogenous substances, and work to increase and retain moisture. However, ceramides are extremely expensive, and it can therefore be prohibitively costly to include a significant proportion of ceramides in a skincare product. Known oat oils typically contain just 1-2% ceramides.

Methods for extracting oil from the oat kernel are known, for example as described in WO2010/104444. Neutral and polar lipids may be separated from oats by extracting the polar lipids using a polar solvent such as ethanol. In some of the fractions obtained by this method, polar lipids form a high proportion of the total lipid content. However, the products produced by this method still contain a substantial amount of solvent and water (typically about 25%) and sugar. In addition, the proportion of desirable skincare components, such as ceramides, phospholipids and sterols, present in the fractions obtained is low.

High levels of solvent and water in the final fractions dilute the end product, thus reducing further the concentration of desirable skincare components. In addition, the presence of a flammable solvent such as ethanol in the end product is undesirable for health and safety reasons.

SUMMARY

There is therefore a need for an extract which contains a significant proportion of desirable skincare components, but which does not contain a significant water/solvent residue. There is also a need for a reliable and economical method of manufacturing such a product.

There has now been developed a product which overcomes or substantially mitigates the problems associated with the prior art.

It has been surprisingly found that a previously unconsidered by-product of the fractionation of oat oil from the oat kernel, which is produced as a viscous residue during the extraction of oil from oats by fractionation with a polar solvent, can be further refined to produce an oat lipid extract which is high in polar lipids, and which is substantially free from solvent.

DETAILED DESCRIPTION

Thus, according to a first aspect of the invention there is provided an oat lipid extract which comprises a neutral lipid fraction and a polar lipid fraction, the polar lipid fraction forming at least 20% w/w of the oat lipid extract, and wherein the oat lipid extract is substantially free from solvent.

The oat lipid extract of the invention is particularly advantageous. Firstly, the oat lipid extract of the invention is substantially free from solvent. This concentrates the desirable skincare components present in the extract, and removes the health and safety concerns surrounding a product containing a significant amount of a flammable solvent. In addition, the extract according to the invention comprises at least 20% w/w polar lipids, that is, at least 20% of the extract is in the form of polar lipids. Many of the polar lipids known to be present in oats are desirable skincare agents, eg ceramides and phospholipids. These skincare agents are generally considered to be difficult and/or extremely expensive to obtain in their refined state for use in cosmetic compositions, and the presence of a high proportion of these polar lipids in the oat extract of the invention is therefore highly desirable. The combination of polar lipids and neutral lipids, moreover, provides a composition which is ideally suited for use in both cosmetic and pharmaceutical skincare.

By "substantially free from solvent" is meant, in the context of the invention, that the oat lipid extract contains very little or no solvent. Specifically, "substantially free from solvent" is intended to mean that the oat lipid extract contains less than 0.5% solvent, more preferably less than 0.1% solvent, or less than 0.01% solvent, even more preferably less than 0.001% solvent.

By "solvent" is meant, in the context of the invention, a liquid which is capable of dissolving the lipid components of the oats. For example, the solvent may be polar, eg methanol or ethanol, or the solvent may be non-polar, eg hexane. Preferably, the solvent is polar. More preferably, the solvent is an alcohol or alcohol/water mixture, most preferably, the solvent is ethanol or an ethanol/water mixture.

Although *Avena sativa* is the oat species most commonly used globally, there are a number of different species of oats, any of which are suitable for producing the oat lipid extract of the invention. These include *Avena atlantica, Avena sativa, Avena byzantina, Avena sterilis, Avena fatua, Avena abyssinica, Avena strigosa, Avena barbata, Avena longiglumis, Avena moraccana, Avena murphyi, Avena prostrata, Avena pilosa, Avena hirtula, Avena mastrostrachya, Avena magna, Avena wiestii, Avena fatua, Avena vaviloviana, Avena nuda, Avena brevis, Avena damascene, Avena lusitanica, Avena canariensis, Avena insulari, Avena agadiriana, Avena eriantha, Avena clauda, Avena ventricosa* and *Avena sativa* naked type. Particularly preferred species are *Avena sativa, Avena sativa* naked type and *Avena strigosa*, particularly *Avena sativa*.

Polar Lipid Fraction

The polar lipid fraction forms at least 20% w/w of the oat lipid extract. That is, at least 20% w/w of the oat lipid extract is made up of polar lipids. For example, the polar lipid fraction may form at least 25% w/w of the oat lipid extract, at least 30% w/w of the oat lipid extract, or more preferably least 35% w/w of the oat lipid extract. The polar lipid fraction may form up to 99% w/w of the oat lipid extract, or up to 95% w/w of the oat lipid extract, or up to 90% w/w of the oat lipid extract. Thus, the polar lipid fraction may form from about 20% w/w to about 99% w/w of the oat lipid extract, from about 25% w/w to about 99% w/w of the oat lipid extract, from about 30% w/w to about 95% w/w of the oat lipid extract, preferably from about 35% w/w to about 95% w/w of the oat lipid extract. It will be understood that the polar lipid fraction may form any proportion of the oat lipid extract within these ranges. Thus, the polar lipid fraction may form 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% w/w of the oat lipid extract.

Depending on the conditions used to refine the oat lipid extract, extracts having different proportions of polar lipids may be produced. Thus, in one embodiment, the polar lipid fraction preferably forms from about 30% to 50% w/w of the oat lipid extract, more preferably from about 35% to 45% w/w of the oat lipid extract, most preferably about 40% w/w of the oat lipid extract.

In another embodiment, the polar lipid fraction preferably forms from about 75% to 95% w/w of the oat lipid extract, more preferably from about 85% to 95% w/w of the oat lipid extract, most preferably about 90% w/w of the oat lipid extract.

The polar lipid fraction preferably comprises galactosyl acyl glycerols.

Galactosyl acyl glycerols, also known as acylgalactosylglycerols, have physical skin moisturising properties and are therefore valuable in the treatment of problems associated with dry skin. It is believed that these compounds moisturise the skin by binding water through hydrogen bonding, which maintains a reservoir of water on or next to the skin.

Galactosyl acyl glycerols may also have peroxisome proliferator-activated receptor (PPAR) activity, which is related to lipid storage and inflammation processes. PPAR activity has not been previously reported in relation to oats or compounds derived from them.

The galactosyl acyl glycerols preferably include monogalacosyldiacylglycerols and diacylgalactosyldiacylglycerols.

Preferably, the oat lipid extract of the invention comprises at least 2% w/w galactosyl acyl glycerols. More preferably, the oat lipid extract comprises at least 4% or at least 5% w/w galactosyl acyl glycerols. Most preferably, the oat lipid extract of the invention comprises at least 6% w/w galactosyl acyl glycerols.

Thus, the oat lipid extract of the invention preferably comprises at least 4% w/w, more preferably at least 6% w/w, of galactosyl acyl glycerols, including one or more monogalacosyldiacylglycerols and/or diacylgalactosyldiacylglycerols.

The polar lipid fraction preferably comprises phospholipids.

Phospholipids are a class of polar lipids which form a major component of cell membranes. They are amphipathic molecules, consisting of a glycerol molecule, two fatty acids, and a phosphate group which is modified by an alcohol. The fatty acid chains are hydrophobic, while the phosphate "head" is hydrophilic. The breakdown of phospholipids is thus a source of free fatty acids.

Phospholipids are important to barrier function, forming a liquid crystal structure which aids the breathable barrier of the skin. They are also an important source of a range of fatty acids, including essential fatty acids such as linoleic acid. Linoleic acid can be derived from the circulation, but may also be recycled within the epidermis. Thus, topically applied phospholipids, which release linoleic acid upon breakdown, are advantageous to barrier development and/or repair.

In addition, phospholipids may form monolayers, and topical treatment with phospholipids acts as a penetration enhancer, disrupting the lamellar organisation of the stratum corneum. This can help deliver the oat lipid extract deep into the skin where it can be metabolised.

The phospholipids present in the oat lipid extract of the invention preferably include one or more of phosphatidyl choline, phosphatidylethanolamine, phosphatidyl glycerol, phosphatidyl serine and/or phosphatidyl inositol.

The oat lipid extract of the invention preferably comprises at least 4% w/w phospholipids, more preferably at least 6%, or at least 8% w/w phospholipids. More preferably, the oat lipid extract comprises at least 9% w/w phospholipids, more preferably the oat lipid extract comprises at least 10% w/w phospholipids, most preferably, the oat lipid extract comprises at least 12% w/w phospholipids.

Thus, the oat lipid extract of the invention preferably comprises at least 9% w/w, more preferably at least 12% w/w, of phospholipids including one or more of phosphatidyl choline, phosphatidylethanolamine, phosphatidyl glycerol, phosphatidyl serine and/or phosphatidyl inositol.

The polar lipid fraction preferably comprises long chain base compounds.

Long chain base compounds, or sphingolipids, are a class of long-chain aliphatic amines containing two or three hydroxyl groups, commonly containing a trans-double bond in position 4.

Long chain base compounds present in the oat lipid extract of the invention may preferably include compounds containing the following long chain bases: sphinganine, sphingosine, 4-hydroxysphinganine, 4-hydroxysphin-8-enine and/or 4,8-sphingadiene.

Long chain base compounds present in the oat lipid extract of the invention may preferably comprise compounds formed from the long chain bases discussed above, combined with a fatty acid, and may include ceramides, glycosyl ceramides, glycosyl hydroxyceramides, glycosylinositophosphoceramides, glycosylinositophosphohydroxyceramides and/or hydroxyceramides.

Ceramides and hydroxyceramides are key components of the stratum corneum lipid membrane. Six forms of ceramide are naturally found in the epidermis, creating a barrier which reduces infection and retains moisture. They are waxy lipid molecules, consisting of a sphingoid (long-chain) or hydroxy-sphingoid base linked to a fatty acid via an amide bond.

As skin ages, ceramide and hydroxyceramide production decreases, resulting in incomplete barrier function and dry itchy skin which lacks suppleness. The ceramides found in skin are identical or substantially equivalent to phyto-derived ceramides which, when applied topically, integrate into the skin barrier layers and are resistant against exogenous substances. The addition of long chain base compounds in the form of ceramides and hydroxyceramides to the skin thus enhances or supplements a reduced level of ceramides in the skin, increasing moisturisation, flexibility and suppleness of the skin.

Glycosyl ceramides and glycosyl hydroxyl ceramides, and more specifically glucosoyl ceramides and glucosoyl hydroxyceramides, are a group of glycosphingolipids consisting of a ceramide with a single glucose residue at the 1-hydroxyl position. They are a major precursor for ceramide synthesis in the skin, and thus support the ceramide function described above.

Glycosylinositolphosphoceramides and glycosylinositolphosphohydroxyceramides, and more specifically glucosylinositolphosphoceramides and glucosylinositolphosphohydroxyceramides are predominantly found in plants and funghi, and have not been previously considered as skincare actives. It is believed that they may have activity as tumour necrosis factor (TNF) suppressors, and hence may contribute to anti-inflammatory activity.

Ceramides, glycosyl ceramides, glycosyl hydroxyceramides, glycosylinisitolphosphoceramides, glycosylinisitolphosphohydroxyceramides and hydroxyceramides are identified by reference to their sphingoid base (long chain base) and attached fatty acid. Both sphingoid base and fatty acid may be noted xx:y, wherein x is the number of carbon atoms and y is the number of double bonds present. In addition, the sphingoid base may be prefixed by either "d" or "t", indicating a dihydroxy or trihydroxy base respectively.

Thus, a long chain base compound with a d18:1 long chain base and attached 16:0 fatty acid refers to a compound in which sphingosine and palmitic acid are linked via an amide bond.

Particular ceramides, glycosyl ceramides, glycosyl hydroxyceramides, glucosylinositophosphoceramides glycosylinisitolphosphohydroxyceramides and hydroxyceramides present in the oat lipid extract of the invention are those with long chain bases d18:0, d18:1, d18:2, t18:0 and t18:1, and $C_{16}$-$C_{26}$ saturated and unsaturated fatty acids. Particular fatty acids are 16:0, 18:0, 20:0, 22:0, 24:0, 26:0, 20:1, 22:1, 24:1 and 26:1. It will be understood that in some cases the fatty acids may be hydroxy fatty acids.

Thus, for example, ceramides, glycosyl ceramides, glycosyl hydroxyceramides, glycosylinositolphosphohydroxyceramides, glycosylinositophosphoceramides and hydroxyceramides present in the invention may have any of the following combinations of long chain base (LCB) and attached fatty acid (FA)

| LCB | FA |
|---|---|
| d18:0 | 16:0 |
| d18:0 | 18:0 |
| d18:0 | 20:0 |
| d18:0 | 20:1 |
| d18:0 | 22:0 |
| d18:0 | 22:1 |
| d18:0 | 24:0 |
| d18:0 | 24:1 |
| d18:0 | 26:0 |
| d18:0 | 26:1 |
| d18:1 | 16:0 |
| d18:1 | 18:0 |
| d18:1 | 20:0 |
| d18:1 | 20:1 |
| d18:1 | 22:0 |
| d18:1 | 22:1 |
| d18:1 | 24:0 |
| d18:1 | 24:1 |
| d18:1 | 26:0 |
| d18:1 | 26:1 |
| d18:2 | 16:0 |
| d18:2 | 18:0 |
| d18:2 | 20:0 |
| d18:2 | 20:1 |
| d18:2 | 22:0 |
| d18:2 | 22:1 |
| d18:2 | 24:0 |
| d18:2 | 24:1 |
| d18:2 | 26:0 |
| d18:2 | 26:1 |
| t18:0 | 16:0 |
| t18:0 | 18:0 |
| t18:0 | 20:0 |
| t18:0 | 20:1 |
| t18:0 | 22:0 |
| t18:0 | 22:1 |
| t18:0 | 24:0 |
| t18:0 | 24:1 |
| t18:0 | 26:0 |
| t18:0 | 26:1 |
| t18:1 | 16:0 |
| t18:1 | 18:0 |
| t18:1 | 20:0 |

-continued

| LCB | FA |
|---|---|
| t18:1 | 20:1 |
| t18:1 | 22:0 |
| t18:1 | 22:1 |
| t18:1 | 24:0 |
| t18:1 | 24:1 |
| t18:1 | 26:0 |
| t18:1 | 26:1 |

Particular ceramides which may be present in the oat lipid extract of the invention are:
 ceramide NS (previous nomenclature: ceramide 2; formed of non-hydroxy fatty acids and 4-sphingenines),
 ceramide NP (previous nomenclature: ceramide 3; non-hydroxy fatty acids and 4-hydroxysphinganines),
 ceramide EOH (previous nomenclature: ceramide 4; ester-linked non-hydroxy fatty acids, ω-hydroxy fatty acids and 6-hydroxy-4-sphingenines),
 ceramide AS (previous nomenclature: ceramide 5; α-hydroxy fatty acids and 4-sphingenines) and
 ceramide AP (previous nomenclature: ceramide 6; α-hydroxy fatty acids and 4-hydroxysphinganine).

Thus, the oat lipid extract of the present invention preferably comprises one or more long chain base compounds containing a long chain base, the long chain base being selected from sphinganine, sphingosine, 4-hydroxysphinganine, 4-hydroxysphin-8-enine and/or 4,8-sphingadiene.

The oat lipid extract of the invention preferably comprises one or more long chain base compounds selected from ceramides, glycosyl ceramides, glycosyl hydroxyceramides, glycosylinositophosphoceramides glycosylinositophosphohydroxyceramides and/or hydroxyceramides. More preferably, the oat lipid extract of the invention comprises ceramides, glucosyl ceramides, glucosyl hydroxyceramide, glucosylinositophosphoceramides glucosylinositophosphohydroxyceramides and hydroxyceramides The oat lipid extract of the present invention preferably comprises at least 3% w/w long chain base compounds, more preferably at least 4% w/w long chain base compounds.

Thus, the oat lipid extract of the present invention preferably comprises at least 4% w/w long chain base compounds including one or more of sphinganine, sphingosine and/or 4-hydroxysphinganine. More preferably, the oat lipid extract of the invention comprises at least 4% w/w long chain base compounds including one or more of ceramides, glucosyl ceramides, glucosyl hydroxyceramides glycosylinositophosphoceramides, glycosylinositophosphohydroxyceramides and/or hydroxyceramides.

The oat lipid extract of the present may comprise ceramides, glucosyl hydroxyceramides, glycosylinositophosphohydroxyceramides and hydroxyceramides. Preferably, these components are present in molar ratios of about 1:2:2:1, plus or minus 25%.

Thus, the polar lipid fraction may comprise galactosyl acyl glycerols, phospholipids and/or long chain base compounds.

The oat lipid extract preferably comprises at least 6% w/w galactosyl acyl glycerols, at least 9% w/w phospholipids, and at least 4% long chain base compounds.

More preferably, the oat lipid extract of the invention comprises:
 a) at least 6% w/w of galactosyl acyl glycerols, including one or more of monogalacosyldiacylglycerols and diacylgalactosyldiacylglycerols;
 b) at least 9% w/w, more preferably at least 12% w/w, phospholipids, including one or more of phosphatidyl choline, phosphatidylethanolamine, phosphatidyl glycerol, phosphatidyl serine and/or phosphatidyl inositol; and
 c) at least 4% w/w long chain base compounds, including one or more of ceramides, glucosyl ceramides, glucosyl hydroxyceramides glycosylinositophosphoceramides, glycosylinositophosphohydroxyceramides and/or hydroxyceramides.

Many commercial oat oils and extracts contain a significant proportion of the polar lipids monogalactosyldiacylglycerol (MGDG) and digalactosyldiacylglycerol (DGDG).

Galactolipids, including mono- and digalactosyldiacylglycerol, have also been shown to mediate cyclooxygenase enzyme in the arachidonic acid cascade of inflammation. MGDG has, in addition, a cell anti-proliferative activity, but it does not interfere with cell differentiation. Galactolipids have been reported to possess novel cancer chemopreventive effects by suppressing inflammatory mediators.

The oat lipid extract of the present invention preferably contains less than 20% w/w total DGDGs and MGDGs, more preferably less than 15% w/w total DGDGs and MGDGs, eg from 1-15% total DGDGs and MGDGs.

Neutral Fraction

The neutral fraction may form from about 1% w/w to about 80% w/w of the oat lipid extract. For example, the neutral fraction may preferably form from about 5% w/w to about 75% w/w of the oat lipid extract, from about 5% w/w to about 70% of the oat lipid extract, or more preferably from about 5% w/w to about 65% w/w of the oat lipid extract. It will be understood that the neutral lipid fraction may form any proportion of the oat lipid extract within these ranges. Thus, the neutral lipid fraction may form 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79% or 80% w/w of the oat lipid extract.

In one embodiment, the neutral lipid fraction preferably forms from about 50% to 70% w/w of the oat lipid extract.

In another embodiment, the polar lipid fraction preferably forms from about 1% to 15% w/w of the oat lipid extract.

The neutral lipid fraction preferably comprises triacyl glycerols.

A triacyl glycerol, or triglyceride, is an ester derived from glycerol and three fatty acids. They are the main constituents of body fat in humans and animals, and are a major component of human skin oils. Many triglycerides have good emollient and skin-replenishing properties, which can help to rejuvenate the surface of the skin and resist further moisture loss.

The neutral lipid fraction preferably comprises sterols.

Sterols, or steroid alcohols, are a subgroup of steroids. They are amphipathic lipids, which are found in all animal and vegetal tissues. Sterols contribute to overall skin well-being, most notably to resilience and barrier function. They can also act as surfactants, and to provide lubrication to a cosmetic or pharmaceutical product.

The sterols present in the neutral lipid fraction preferably include one or more of delta-5-avenasterol, beta-sitosterol, campesterol, 24-methylene cholesterol, capestanol, stigmasterol, delta-7-campesterol, delta-5,23-stigmastadienol, clerosterol, sitostanol, delta-5,24-stigmastadienol, delta-7-stigmastenol and/or delta-7-avenasterol.

More preferably, the sterols present in the extract of the invention comprise delta-5-avenasterol, beta-sitosterol and/or campesterol.

Preferably, the neutral lipid fraction contains at least 3% w/w sterols.

Thus, the neutral lipid fraction may preferably comprise triacyl glycerols and sterols. More preferably, the neutral lipid fraction comprises triacyl glycerols and sterols, wherein the sterols include one or more of delta-5-avenasterol, beta-sitosterol, campesterol, 24-methylene cholesterol, capestanol, stigmasterol, delta-7-campesterol, delta-5,23-stigmastadienol, clerosterol, sitostanol, delta-5,24-stigmastadienol, delta-7-stigmastenol and/or delta-7-avenasterol. Most preferably, the sterols present in the extract of the invention comprise delta-5-avenasterol, beta-sitosterol and/or campesterol Preferably, when both phospholipids and sterols are present in the oat lipid extract of the invention, the phospholipids and sterols are present in a molar ratio of about 3:2, plus or minus 25%.

In the oat lipid extract of the invention, the polar lipid fraction thus preferably comprises galactosyl acyl glycerols, phospholipids and long chain base compounds, and the neutral lipid fraction preferably comprises triacylglycerols and sterols. The long chain base compounds may particularly comprise ceramides, glycosyl ceramides, glucosylinositophosphoceramides and/or hydroxyceramides, and the sterols may particularly comprise delta-5-avenasterol, sitosterol and/or campesterol.

The oat lipid extract of the invention may also contain other components, either removed from the oat kernel as part of the extraction process, or added to the lipid extract after extraction. In particular, the oat lipid extract may contain a proportion of pigmented material. For example, the oat lipid extract may contain from 0% to 10% w/w pigmented material, or from 0.1% to 8% w/w pigmented material, or from 2% to 6% w/w pigmented material, or from 3% to 5% w/w pigmented material. Preferably, the oat lipid extract of the invention comprises from 0% to 10% w/w, more preferably from 2% to 6% w/w pigmented material.

The compounds described above which may be present in the oat lipid extract according to the invention all have substantial skincare benefits, and the combination of some or all of these components provides a unique combination of benefit agents for addition to skincare products. Some of the components, particularly ceramides, are very expensive to purchase as refined ingredients. The presence of a significant quantity of these components in the oat lipid extract is therefore particularly advantageous, as it enables them to be used in cosmetic and pharmaceutical products in a much more economical manner.

The oat lipid extract of the invention may also contain additional components. These may include, but are not limited to, free fatty acids, wax esters, sterol esters and/or glycolipids.

Method of Manufacture

The oat lipid extract of the present invention is derived from oats. As previously discussed, it has been surprisingly discovered that a previously unconsidered by-product produced during the extraction of oat oil can be further refined, resulting in an oat lipid extract which is high in polar lipids and substantially free from solvent.

The extraction of oat oil from the oat kernel is known, and may be carried out by any suitable method known in the art. In particular, the extraction of oat oil from the oat kernel may be carried out by the method described in WO2010/104444.

Oil from oat kernels may be obtained through extraction with a solvent, eg supercritical $CO_2$, hexane or an aliphatic alcohol. The raw oat groats are first milled and sieved, before being mixed with an excess of solvent. The oat and solvent mixture may then be placed in a centrifuge, in order to remove the solid components. The solvent is evaporated from the remaining fluid, and can be returned to the extraction stage and reused. The crude oil remaining after evaporation has a high ethanol and sugar content.

It has been found that the use of a non-polar solvent, such as hexane, results in a crude oil containing lipids, starch and proteins, small amounts of water and traces of hexane. However, the lipids extracted are largely the neutral lipids, with only small amounts of polar lipids observed.

The use of a polar solvent, such as an alcohol or alcohol/water, results in a crude oat oil containing lipids, a large amount of sugar, some insoluble starch and solvent. Due to the polar solvent, a large proportion of polar lipids are observed in the crude oil.

Preferably, the oil is extracted using a polar solvent. Preferably the polar solvent is an alcohol or an alcohol/water mixture. More preferably, the polar solvent is ethanol or an ethanol/water mixture.

The crude oil may be further fractionated using a polar solvent, in order to produce fractions containing difference concentrations of solvent, lipids and sugars.

As a result of this fractionation process, a previously unconsidered residue is produced as a by-product. This residue is sticky and viscous in nature, and consequently difficult to work with. Despite being produced as a by-product of the oat oil industry for years, it has been disposed of as a waste product. It has now surprisingly been discovered that this waste product contains a high proportion of desirable skincare actives, and it has further been discovered that this residue may be refined in the following manner, to make it useable in skincare compositions.

First, a solvent/water fractionation is carried out on the residue, in order to concentrate the desirable compounds. Preferably, a polar solvent is used. More preferably, the solvent is ethanol, or an ethanol/water mixture.

Following fractionation, the solvent and water present in the fraction are removed. Preferably, they are removed using an evaporator, more preferably using a wiped film evaporator. A wiped film evaporator comprises a cylindrical heated body and a rotor. The fraction enters the heated body at the top, and is evenly distributed over the inner surface of the evaporator by the rotor. Volatile components are rapidly evaporated, while non-volatile components are discharged at the outlet. The short residence time of a substance within the evaporator, coupled with the high turbulence from the rotor, enables this process to be used with heat sensitive, viscous fluids which are difficult to refine by other methods.

Thus, according to a second aspect of the invention there is provided a method of manufacturing the oat lipid extract of any preceding claim, comprising:
 a) taking a waste product produced as a by-product during the multi-stage solvent fractionation of oats;
 b) carrying out solvent/water fractionation on the waste product to produce an extract;
 c) removing the solvent and water from the extract.

In an alternative process, the extract may be refined using a multi effect evaporator. Following this, stripping, drying and filtration processes are carried out on the oil. Finally, the solvent is extracted.

Where drying or evaporation of an extract or fraction is required during manufacture, this process preferably takes place under vacuum. This is advantageous as it allows drying to take place at lower temperatures. In addition, certain components, eg phospholipids, "hold onto" solvents (particularly water), and drying under vacuum aids in more complete removal of these solvents.

The oat lipid extract obtained by this process is substantially free of solvent. Preferably, the oat lipid extract obtained by this process is substantially free of solvent and water, eg ethanol and water. The absence of solvent and, preferably, water in the extract concentrates the desirable skincare components. In addition, many polar solvents, such as ethanol, are flammable and their presence in the oat lipid extract would therefore carry safety risks.

Preferably, the oat lipid extract of the invention is substantially free of sugars and starches. By "sugars" is meant, in the context of the invention, free sugars eg glucose, fructose and sucrose, as well as polysaccharides and celluloses. The term "sugars" is not intended to include saccharide groups which are present as functional groups on other compounds.

The removal of additional, undesirable components, such as sugars and starches, further concentrates the desirable skincare components present in the extract. This results in a higher proportion of the desirable compounds, eg ceramides, phospholipids and sterols.

Uses

The high proportion of polar lipids in the oat lipid extract of the present invention make it particularly suitable for use in cosmetic and pharmaceutical applications intended for topical application to the skin. Many of the polar lipids known to be present in oats are desirable skincare agents, eg ceramides and phospholipids, having soothing and barrier enhancing properties. These skincare agents may be difficult or extremely expensive to obtain in their refined state for use in cosmetic compositions, and the presence of a high proportion of these polar lipids in the oat extract of the invention is therefore highly desirable.

Thus, according to a third aspect of the invention there is provided a composition comprising an oat lipid extract which comprises a neutral lipid fraction and a polar lipid fraction, the polar lipid fraction forming at least 20% w/w of the oat lipid extract, and wherein the oat lipid extract is substantially free from solvent.

It will be understood that any of the features described above in relation to first aspect of the invention may be present in the third aspect of the invention.

The composition of the third aspect may contain at least 0.05% oat lipid extract. The composition may contain less than 10% oat lipid extract. For example, the composition of the third aspect may comprise from 0.05-10% w/w of the oat lipid extract, or from 0.1-5% w/w of the oat lipid extract, or from 0.1-2% w/w of the oat lipid extract.

The composition of the third aspect of the invention may be a cosmetic or pharmaceutical composition, and may particularly be a cosmetic, toiletry or topical healthcare product.

The oat lipid extract of the invention may be used in skincare compositions for the alleviation of dry skin, dry or chapped lips, dry hair, skin barrier enhancement, skin barrier repair, PPAR activation, psoriasis, eczema, sunburn, skin redness, skin irritation, skin itchiness, dry/itchy legs, aged skin treatment, scar prevention, stretch mark prevention and reduction, wound healing, collagen and elastin repair and/or ichthyosis.

The oat lipid extract of the invention may also be used in cosmetic compositions for use on aged skin, and/or in antiaging products, or other products intended to make the skin look and feel good.

The gentle nature of the extract, and the moisturising effects of the extract, make it suitable for use in baby products and in products for sensitive skin, and for use in treatments for dry scalp and/or hair.

A cosmetic or pharmaceutical composition containing the oat lipid extract of the invention may further comprise one or more additional active components. Any additional components used should be suitable for use in contact with human skin tissue without undue toxicity, instability, allergic reaction and the like. For example, compositions may contain anti-acne actives, anti-bacterial agents, anti-inflammatory agents, anti-irritant agents, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, peptides, herbal extracts, conditioning agents, moisturising agents, emollients, astringent or antiperspirant compounds, biocidal compounds, sunscreens or UV absorbers, pigments, perfumes, anti-aging agents, enzymes, proteins, vitamins or other useful skin care agents.

The Personal Care Product Council's International Cosmetic Ingredient Dictionary and Handbook, Thirteenth Edition, also describes range of cosmetic and pharmaceutical ingredients which are commonly used in the skin care industry, and which are suitable optional components for use in the compositions of the present invention. These include: abrasives, absorbents, aesthetic components such as fragrances, pigments, colourings/colorants, essential oils, anti-caking agents, antifoaming agents, antimicrobials, binders, biological additives, buffering agents, bulking agents, chelating agents, chemical additives, colorants, cosmetic astringents, cosmetic biocides, denaturants, drug astringents, emollients, external analgesics, film formers or materials, opacifying agents, pH adjusters, preservatives, propellants, reducing agents, sequestrants, skin cooling agents, skin protectants, thickeners viscosity modifiers, vitamins, or combinations thereof.

Compositions comprising the oat lipid extract of the invention may further comprise a dermatologically acceptable carrier. The carrier may, for example, be in the form of a solution, emulsion, or solid form, and a suitable carrier may be selected depending on the desired product.

There is thus provided a cosmetic composition comprising an oat lipid extract according to the invention, the composition further comprising one or more additional active ingredients selected from anti-acne actives, anti-bacterial agents, anti-inflammatory agents, anti-irritant agents, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, peptides, herbal extracts, conditioning agents, moisturising agents, emollients, astringent or antiperspirant compounds, biocidal compounds, sunscreens or UV absorbers, pigments, perfumes, anti-aging agents, enzymes, proteins, vitamins or other useful skin care agents.

The conditioning agents which can be used include polyquatemium, such as the copolymer of N,N'-bis((dimethylamino)-3 propyl)urea and oxy-1,1'bis(2-chloro)ethane; polyquaternium-2, the copolymer of diallyldimethyl ammonium chloride and acrylamide; or polyquaternium-7; cationic polysaccharide derivatives such as cocodimonium hydroxyethyl cellulose; guar hydroxypropyl trimonium chloride; and hydroxypropyl guar hydroxypropyl trimonium chloride.

Suitable moisturising agents include glycerol, sorbitol, urea, collagen, gelatine, aloe vera, hyaluronic acid.

Suitable emollients include alkylmonoglycerides, alkyldiglycerides, triglycerides such as oils extracted from plants and from vegetables (eg coprah oil, palm oil, cottonseed oil, soya bean oil, olive oil, sunflower seed oil, grapeseed oil, peanut oil, sesame oil, castor oil) or oils of animal origin (eg tallow), derivatives of the above oils such as hydrogenated oils, lanolin derivatives, mineral oils or paraffin oils, perhydrosqualane, squalene, diols such as 1,2-propanediol, 1,3-butanediol, cetyl alcohol, stearyl alcohol, oleic alcohol, polyethylene glycols or polypropylene glycols, fatty esters such as isopropyl palmitate, 2-ethylhexyl cocoate, myristyl myristate, esters of lactic acid, stearic acid, behenic acid, isostearic acid, silicone oils such as polydimethylsiloxanes, silicone copolyols (dimethicone copolyol, cetyldimethicone copolyol), diphenyldimethicones, phenyltrimethicones, dimethiconols.

Suitable astringent or antiperspirant compounds include organic or inorganic aluminium, zirconium, zinc salts or their mixed salts or mixtures thereof. These include aluminium chloride, aluminium and/or zirconium hydrochlorides, aluminium chlorhydrex, aluminium-zirconium chlorhydrex glycine, aluminium sulphate, zinc sulphate, zirconium and aluminium chlorohydroglycinate, zirconium hydroxychloride, zirconium and aluminium lactate, aluminium and potassium sulphate, aluminium and sodium chlorohydroxylactate, aluminium hydrobromide, zinc sulphocarbonate, aluminium bromide, and zinc phenolsulphonate associated with aluminium sulphate.

Suitable sunscreen agents and UV filters are known in the art and include both inorganic and organic sunscreens. Inorganic sunscreens include microfine titanium dioxide, microfine zinc oxide, iron oxides, talcs and boron nitride. Organic sunscreen agents include:
  a) p-aminobenzoic acids, esters and derivatives thereof, for example, 2-ethylhexyl p-dimethylaminobenzoate and the octyl ester of p-aminobenzoic acid;
  b) methoxycinnamate esters such as 2-ethylhexyl p-methoxycinnamate, 2-ethoxyethyl p-methoxycinnamate or α,β-di-(p-methoxycinnamoyl)-α'-(2-ethylhexanoyl)-glycerin;
  c) benzophenones such as oxybenzone;
  d) 2-phenylbenzimidazole-5-sulfonic acid and disodium phenyl dibenzimidazole tetrasulfonate and terphthalylidene dicamphor sulfonic acid;
  e) alkyl-β,β-diphenylacrylates, for example alkyl α-cyano-β,β-diphenylacrylates such as octocrylene;
  f) triazines such as 2,4,6-trianilino-(p-carbo-2-ethylhexyl-1'-oxy)-1,3,5 triazine and bis-octyloxyphenol methoxyphenyl triazine;
  g) camphor derivatives such as methylbenzylidene camphor;
  h) organic pigment sunscreening agents such as methylene bis-benzotriazole tetramethyl butylphenol;
  i) silicone derivatives such as drometrizole trisiloxane, benzylidene malonate polysiloxane and dimethicodiethyl benzal malonate
  k) salicylates such as octyl salicylate; and
  l) Organic nano particles such as Methylene Bis-Benzotriazolyl Tetramethylbutylphenol Suitable perfumes include benzaldehyde, caraway oil, cardamon oil, cinnamon oil, ethylvanilin, eucalyptus globulus oil, glutamic acid, clove oil, orange oil, peppermint oil, thymol, phenethyl alcohol or their mixtures.

Suitable anti-aging agents include carrot extract, Ceramide 33 and hydrolyzed serum protein.

Suitable enzymes include lipase, papain, soy protein and coenzymes such as ubiquinone Q10.

Suitable proteins include collagen, collagen derivatives and keratin.

Suitable vitamins include retinol, retinyl palmitate, tocopherol, tocopherol acetate, menadione, ascorbic acid and ascorbyl palmitate.

The oat lipid extract of the invention may be formulated with a carrier and provided in a delivery system. This would make the extract easier to handle and to use in formulations.

Thus, according to a fourth aspect of the invention, there is provided a delivery system, the delivery system comprising the oat lipid extract of the first aspect of the invention and a carrier. It will be understood that any of the features described in relation to the oat lipid extract of the first aspect of the invention may be present.

Suitable carriers for use in delivery systems are known in the art, and the oat lipid extract may be formulated in any suitable manner, depending on the properties required in the final formulation.

In particular, the carrier may be glycerine or glycol. Preferably, the ratio of oat lipid extract to glycerine and/or glycol is from 1:1 to 1:4. Such a formulation stabilises the oat lipid extract, enabling easy addition into emulsion systems.

Alternatively, where cold water dispersibility is important, the oat lipid extract of the invention may be blended with a carrier selected from polysorbate-20, polysorbate-60 and polysorbate-80. Preferably, the oat lipid extract and carrier are in a ratio of from 1:1 to 1:4.

A further suitable carrier, providing cold water dispersibility and stability, is a cyclic oligosaccharide, eg cyclodextrin. In this case, the oat lipid extract and carrier are preferably in a ratio of 1:1.

The oat lipid extract of the invention may alternatively be incorporated into an emulsion or microemulsion, for example into a Malvern-type microemulsion or Evonik-type phase-inversion emulsion. The oat lipid extract may be present at about 30-40% w/w.

The oat lipid extract may also be suspended in a xanthan gum emulsion system, to provide increased cold water dispersibility.

Presenting the extract in a form that will aid solubilisation will help the extract to be effectively included in products. Solubilisers with a high HLB (Hydrophile-Lipophile Balance) are preferred, as they balance the low HLB of the phospholipids and other components which may be present in the oat lipid extract. Suitable solubilisers for use as the carrier in the delivery system of the invention include:
  polysorbate-80 (eg Tween 80);
  sucrose esters such as sucrose palmitate (eg Sisterna PS-750C) or sucrose laurate (eg Sisterna L70-C);
  polyglyercyl-4 laurate/sebacate and polyglyceryl-6 caprylate/caprate (NatraGem™ S140NP);
  a combination of caprylyl/capryl glucoside, polyglyceryl-10 laurate, babassu oil polyglyceryl-4 esters, and citric acid (Resassol Ultimate);
  Polyglyceryl-6 caprylate, polyglyceryl-3 cocoate, polyglyceryl-4 caprate, polyglyceryl-6 ricinoleate (Tego Solve 61);
  Heptyl glucoside (Sepiclear G7).

Preferably, the solubiliser is present in an amount from 50-75% w/w of the delivery system.

The invention will now be illustrated, by way of example only, with reference to the following Examples.

Example 1

Fatty Acid Composition

Without intending to limit the scope of the invention in any way, three example oat lipid extracts (Batches 1, 2 and 3) according to the invention are provided in Table 1 below. Table 2 shows the breakdown of the fatty acid composition of the same three oat lipid extracts.

TABLE 1

Oat lipid extract composition of oils (%)

| LIPID CLASS | SAMPLE ID | | |
|---|---|---|---|
| | Batch 1 | Batch 2 | Batch 3 |
| Triacylglycerols | 37.0 | 33.4 | 32.5 |
| Free fatty acids | 11.4 | 8.8 | 8.3 |
| Cholesterol/sterols | 9.5 | 7.7 | 7.7 |
| Diacylglycerol | 2.1 | 2.6 | 2.5 |
| Total neutral lipids | 60.0 | 52.5 | 51.0 |

TABLE 1-continued

Oat lipid extract composition of oils (%)

| LIPID CLASS | SAMPLE ID | | |
|---|---|---|---|
| | Batch 1 | Batch 2 | Batch 3 |
| Monogalactosyldiacylglycerols | 2.4 | 3.0 | 3.5 |
| Digalactosyldiacylglycerols | 7.2 | 8.2 | 8.6 |
| Total galactoacylglycerols | 9.6 | 11.2 | 12.1 |
| Unknown glycolipid* | 6.3 | 9.5 | 8.1 |
| Long Chain Base compounds | 4.0 | 4.4 | 6.0 |
| Sulpholipids | 0.6 | 0.8 | 1.6 |
| Phosphatidylethanolamine | 2.9 | 3.9 | 4.0 |
| Phosphatidylglycerol | 1.2 | 1.1 | 1.3 |
| Phosphatidylinositol | 3.6 | 4.6 | 4.1 |
| Phosphatidylserine | 0.8 | 1.1 | 0.7 |
| Phosphatidylcholine | 6.0 | 6.0 | 6.5 |
| Lysophosphatidylcholine | 1.0 | 1.0 | 1.1 |
| Total Phospholipids | 15.5 | 17.7 | 17.7 |
| Pigmented material | 4.0 | 3.9 | 3.5 |
| Total polar lipids | 40.0 | 47.5 | 49.0 |

*May contain long chain base compounds
Above values calculated from analyses performed in duplicate, as determined by HPTLC

TABLE 2

Fatty acid composition (% total fatty acids and mg FA.100 g$^{-1}$) of total lipid from oat extract

| | Batch 1 | | Batch 2 | | Batch 3 | |
|---|---|---|---|---|---|---|
| Fatty acid | % | mg. 100 g$^{-1}$ | % | mg. 100 g$^{-1}$ | % | mg. 100 g$^{-1}$ |
| Saturates | | | | | | |
| 14:0 | 0.22 | 192.00 | 0.21 | 186.00 | 0.18 | 152.00 |
| 15:0 | 0.10 | 86.00 | <LOQ | <LOQ | <LOQ | <LOQ |
| 16:0 | 17.31 | 15038.00 | 17.09 | 14813.00 | 16.97 | 14641.00 |
| 18:0 | 1.90 | 1654.00 | 1.82 | 1580.00 | 1.68 | 1447.00 |
| 20:0 | 0.13 | 115.00 | 0.15 | 127.00 | 0.11 | 95.00 |
| 22:0 | 0.10 | 88.00 | 0.11 | 94.00 | 0.12 | 107.00 |
| 24:0 | 0.11 | 92.00 | 0.11 | 97.00 | 0.11 | 98.00 |
| Total saturated | 19.87 | 17265.00 | 19.49 | 16897.00 | 19.17 | 16540 |
| Monounsaturate | | | | | | |
| 16:1n-9 | 0.06 | 53.00 | <LOQ | <LOQ | 0.06 | 51.00 |
| 16:1n-7 | 0.24 | 207.00 | 0.20 | 171.00 | 0.26 | 221.00 |
| 18:1n-9 | 38.08 | 33081.00 | 37.30 | 32333.00 | 36.28 | 31302.00 |
| 18:1n-7 | 0.94 | 817.00 | 0.92 | 801.00 | 0.94 | 807.00 |
| 20:1n-9 | 0.65 | 561.00 | 0.64 | 556.00 | 0.64 | 548.00 |
| 22:1n-11 | 0.06 | 53.00 | <LOQ | <LOQ | 0.06 | 49.00 |
| 22:1n-9 | 0.07 | 63.00 | <LOQ | <LOQ | 0.06 | 54.00 |
| 24:1n-9 | 0.08 | 72.00 | 0.06 | 56.00 | 0.07 | 57.00 |
| Total monounsaturated | 40.18 | 34907.00 | 39.12 | 33917.00 | 38.35 | 33089 |
| Polyunsaturates | | | | | | |
| 18:2n-6 | 38.72 | 33639.00 | 39.97 | 34654.00 | 40.99 | 35371 |
| Total n-6 PUFA | 38.72 | 33639.00 | 40.04 | 34708.00 | 40.99 | 35371 |
| 18:3n-3 | 1.22 | 1063.00 | 1.35 | 1168.00 | 1.49 | 1285.0 |
| Total n-3 PUFA | 1.22 | 1063.00 | 1.35 | 1168.00 | 1.49 | 1285.0 |
| Total PUFA | 39.95 | 34702.00 | 41.38 | 35876.00 | 42.48 | 36656 |
| Total | 100.00 | 86874.00 | 100.00 | 86690.00 | 100.00 | 86285 |

Example 2

Relative Molar Concentration of Long Chain Base Compounds

Tables 3-6 show the relative molar concentration of certain long chain base compounds which may be present in an embodiment of an oat lipid extract according to the invention.

TABLE 3

Relative molar concentration of ceramides

| | c16:0 | c18:0 | c20:0 | c20:1 | c22:0 | c22:1 | c24:0 | c24:1 | c26:0 | c26:1 | total |
|---|---|---|---|---|---|---|---|---|---|---|---|
| d18:0 | 0.99 | 0.30 | 0.23 | 0.30 | 0.05 | 0.02 | 0.02 | 0.33 | 0.16 | 0.23 | 2.67 |
| d18:1 | 0.68 | 2.09 | 5.20 | 16.75 | 0.16 | 3.85 | 1.58 | 5.06 | 0.72 | 0.56 | 36.66 |
| d18:2 | 0.53 | 5.40 | 21.16 | 80.48 | 2.69 | 33.25 | 4.62 | 55.90 | 3.21 | 9.54 | 216.79 |
| t18:0 | 23.19 | 1.62 | 2.22 | 14.22 | 6.93 | 3.05 | 8.86 | 3.83 | 2.05 | 0.85 | 66.81 |
| t18:1 | 7.29 | 1.70 | 1.03 | 0.48 | 2.34 | 2.63 | 6.99 | 8.92 | 6.87 | 1.49 | 39.74 |
| Total | | | | | | | | | | | 362.65 |

TABLE 4

Relative molar concentration of hydroxyceramides

| | h16:0 | h18:0 | h20:0 | h20:1 | h22:0 | h22:1 | h24:0 | h24:1 | h26:0 | h26:1 | total |
|---|---|---|---|---|---|---|---|---|---|---|---|
| d18:0 | 0.22 | 0.43 | 1.26 | 0.04 | 0.13 | 0.00 | 0.00 | 0.31 | 0.00 | 0.17 | 2.81 |
| d18:1 | 0.84 | 4.18 | 13.61 | 1.05 | 0.71 | 0.58 | 2.42 | 2.24 | 0.61 | 0.50 | 26.73 |
| d18:2 | 0.36 | 6.73 | 13.61 | 0.70 | 3.71 | 1.29 | 13.86 | 13.40 | 2.19 | 0.71 | 56.56 |
| t18:0 | 0.12 | 0.16 | 1.03 | 0.89 | 1.82 | 2.39 | 3.99 | 9.43 | 1.10 | 0.49 | 21.40 |
| t18:1 | 0.38 | 2.12 | 14.78 | 0.64 | 17.71 | 11.08 | 65.61 | 77.71 | 12.87 | 4.31 | 207.20 |
| Total | | | | | | | | | | | 314.71 |

TABLE 5

Relative molar concentration of Glycoinosotolphosphohydroxyceramides

| | h16:0 | h18:0 | h20:0 | h20:1 | h22:0 | h22:1 | h24:0 | h24:1 | h26:0 | h26:1 | total |
|---|---|---|---|---|---|---|---|---|---|---|---|
| d18:0 | 0.18 | 1.41 | 3.32 | 1.44 | 31.09 | 5.55 | 5.55 | 51.20 | 19.66 | 18.44 | 224.32 |
| d18:1 | 0.34 | 0.52 | 4.04 | 0.46 | 15.60 | 1.38 | 144.00 | 29.23 | 51.86 | 8.38 | 255.80 |
| d18:2 | 0.24 | 0.29 | 0.46 | 0.18 | 1.89 | 1.82 | 29.23 | 0.39 | 8.38 | 0.67 | 43.54 |
| t18:0 | 0.03 | 1.18 | 1.71 | 1.17 | 23.09 | 9.69 | 66.06 | 35.20 | 6.29 | 9.21 | 153.63 |
| t18:1 | 0.05 | 0.07 | 0.78 | 0.43 | 6.46 | 1.92 | 23.47 | 9.66 | 6.14 | 2.09 | 51.07 |
| Total | | | | | | | | | | | 728.35 |

TABLE 6

Relative molar concentration of glucohydroxyceramides

| | h16:0 | h18:0 | h20:0 | h20:1 | h22:0 | h22:1 | h24:0 | h24:1 | h26:0 | h26:1 | total |
|---|---|---|---|---|---|---|---|---|---|---|---|
| d18:0 | 0.00 | 0.00 | 0.00 | 0.00 | 0.00 | 0.18 | 0.18 | 0.00 | 0.12 | 0.00 | 0.47 |
| d18:1 | 2.83 | 14.35 | 16.41 | 1.58 | 1.99 | 1.97 | 1.89 | 3.33 | 0.23 | 0.36 | 44.94 |
| d18:2 | 5.77 | 31.66 | 95.93 | 17.72 | 9.35 | 2.15 | 17.37 | 19.11 | 2.98 | 10.45 | 212.50 |
| t18:0 | 0.00 | 0.05 | 0.00 | 0.00 | 0.27 | 0.66 | 1.26 | 1.06 | 20.66 | 1.77 | 25.73 |
| t18:1 | 0.77 | 0.76 | 4.05 | 0.17 | 3.56 | 2.04 | 12.07 | 12.20 | 104.17 | 139.39 | 279.16 |
| Total | | | | | | | | | | | 562.80 |

The total relative molar concentration of ceramides:hydroxyceramides:glycoinosotolphosphohydroxyceramides:glucohydroxyceramides was found to be 362.65:314.71:728.35:562.80, or approximately 1:1:2:2 plus or minus 25%.

Example 3

Relative Molar Concentration of Triacyl Glycerols

Table 7 shows the relative molar concentration of certain triacyl glycerols (triglycerides) which may be present in an embodiment of an oat lipid extract according to the invention.

The triacyl glycerols are identified as aa:b, where aa is the total number of carbon atoms present, totaled across all three fatty acids, and b is the total number of unsaturated bonds present in the molecule, totaled across all three fatty acids. For example, 50:0 may refer to triacylglycerols containing the following fatty acids: 16:0, 16:0 and 18:0; 14:0, 16:0 and 20:0; or 12:0, 18:0 and 20:0, or a combination thereof.

TABLE 7

| Relative molar concentration of triacyl glycerols | |
|---|---|
| Triacyl glycerol | Relative molar concentration |
| 50:0 | 0.774574 |
| 50:1 | 6.675146 |
| 50:2 | 9.2691 |
| 50:3 | 0.486569 |
| 50:4 | 0.275321 |
| 52:1 | 6.472534 |
| 52:2 | 34.82523 |
| 52:3 | 46.11117 |
| 52:4 | 25.32127 |
| 52:5 | 1.496301 |
| 54:2 | 9.756363 |
| 54:3 | 36.44999 |
| 54:4 | 50.98948 |
| 54:5 | 46.15601 |
| 54:6 | 20.0131 |
| 54:7 | 1.614618 |
| 54:8 | 0.693199 |
| 54:9 | 2.161055 |
| 55:3 | 4.294183 |
| 55:4 | 4.060005 |
| 55:5 | 1.882723 |
| 56:3 | 1.042337 |
| 56:4 | 1.459553 |
| 56:5 | 0.593865 |
| 56:8 | 0.557249 |
| 56:9 | 2.456518 |

Example 4

Extraction Experiments

Descriptions of a number of experiments used during the development of the refining process for the by-product of commercial oat oil production are provided below.

Crude Oat Oil Wax Residue was recovered from batches of Crude Oat Oil by allowing the barrels to stand in cold storage for up to 3 months. Commercial oat oil was then decanted from the residues. The residue was very dark and not of a commercial standard. A number of extractions were carried out to refine the residue. All samples below were prepared from Crude Oat Oil Wax Residue (OWR). Samples presented from those that generated distinct fractions. All samples were dried using heated rotating thin film evaporator under vacuum. The heating was kept below 50° C., preferably below 40° C.

Experiment 1
OWR degummed with Citric acid/water wash.
Sample 1A:—Top oil layer, light amber thin liquid with slight haze. Yield 44%, polar lipid 11.5%
Sample 1B:—Bottom gum layer, red brown waxy consistency. Yield 56%, high polar lipid 54.2

Sample 1C:—Top oil layer above washed 1:3 with ethanol, light amber liquid refined low polar lipid not analysed
Experiment 2
Whole OWR extracted with Acetone.
Sample 2A:—Top fraction dark amber liquid from which pale wax has settled out. Yield 69% polar lipid 21.6%
Sample 2B:—Bottom fraction straw coloured waxy/rubbery solid Yield 31% high polar lipid and waxes 78%
Experiment 3
Gum fraction 1B from experiment 1 further fractionated with Acetone
Sample 3A:—Top fraction dark amber mobile liquid from which pale wax has settled out. Yield 36%, polar lipid 18.7
Sample 3B:—Bottom fraction brown waxy/rubbery solid. Yield 64% high polar lipid and high wax 71.6%
Experiment 4
Whole OWR was dissolved in ethyl acetate and filtered through C18 resin (typically used to remove peptides and similar polar contaminants. Not immediately commercially viable but could point the way for specific fractionation) Extract method not quantitative so no yield values.
Sample 4A:—Ethyl Acetate insoluble fraction. Brown wax suspended liquid. Polar Lipid 52.5%
Sample 4B:—Material not captured by the resin column. Amber coloured liquid with significant amount of suspended pale wax Polar Lipid 46.6%
Sample 4C:—Material captured by the C18 resin. Pale amber thick liquid Polar Lipid 50.0%
Experiment 5
Whole OWR dissolved into Ethyl Acetate and insoluble material removed. Ethanol then added to the soluble fraction to reduce solubility resulting in two fractions.
Sample 5A:—Top fraction, pale amber waxy liquid. Yield 56%. Polar Lipid 43.3%
Sample 5B:—Bottom fraction, amber waxy liquid. Yield 44% Polar Lipid 47.3%

Example 5

Comparative Data for Oat Lipid Extract and Oat Oil

The oat lipid extract of the invention was compared with standard oat oil in a barrier function and hydration gene array model, using a reconstructed human epidermis model.

Oat lipid extract was applied at a concentration of 0.005%, and oat oil was applied at 0.017%. These concentrations were calculated to deliver the same total concentration of polar lipids, to rule out any concentration effects.

The oat lipid extract and oat oil were applied topically to the model in a water/DMSO/Ethanol carrier. The carrier was also applied as the control. The genes associated with barrier function and hydration were measured using a qPCRarray. The results are provided in Table 8 below.

TABLE 8

| comparative data for oat lipid extract and oat oil | | | |
|---|---|---|---|
| | Gene Stimulation compared to control | | % Increase in gene stimulation by Oat Lipid Complex compared to Oat Oil |
| Gene Markers | Oat Oil (0.017%) | Oat Lipid Complex (0.005%) | |
| Inflammation - IL8 | 70 | 114 | 162.9 |
| Keratin Differentiation - trychohyalin | 87 | 155 | 178.2 |

TABLE 8-continued comparative data for oat lipid extract and oat oil

| Gene Markers | Gene Stimulation compared to control | | % Increase in gene stimulation by Oat Lipid Complex compared to Oat Oil |
|---|---|---|---|
| | Oat Oil (0.017%) | Oat Lipid Complex (0.005%) | |
| Keratin Differentiation - repetin | 69 | 115 | 166.7 |
| Adherens Junction - occludin | 81 | 137 | 169.1 |
| Extracellular Matrix - hyaluronan synthase 3 | 83 | 225 | 271.1 |

In this assay, gene stimulation below 100 cannot be considered as an up-regulation of the gene. Only the oat lipid extract of the invention shows up-regulation. Up-regulation of hyaluronan Synthase 3 is particularly significant for skincare products as hyaluronic acid is a key part of the skin's natural moisturising factor.

This data shows that the oat lipid extract showed a surprising increase in performance in key gene marker assays when compared to standard oat oil.

Example 6

Formulations

Intended for illustration purposes only, and not to limit the invention in any way, examples of product formulations containing the oat lipid extract of the invention are provided below:

1. BB Cream

Multi-functional BB cream, a make-up effect light cream with skin-care benefits. The result is a bright, even and mattified skin tone whilst minimising appearance of skin unevenness.

Method:
1. Add materials from phase A to the water with stirring and heat to 70° C.
2. In a separate vessel, premix phase B and heat to 70° C. until melted and uniform
3. Add phase C to phase B with high speed stirring
4. Using a homogeniser, and add the combined phase C and B to phase A and shear for 2-3 minutes until uniform
5. Add phase D and continue to shear until the emulsion is viscous, bright and uniform.
6. Commence cooling with constant stirring to ambient temperature
7. Make to weight with purified water, record pH and viscosity.

| Phase | Common/Trade Name | Supplier | % w/w |
|---|---|---|---|
| A | Oat ® SILK 12 | Oat ® Cosmetics | 2.00 |
| | Disodium EDTA | Various | 0.05 |
| | Glycerin | Various | 3.00 |
| | Euxyl PE9010 | Schulke & Mayr | 1.00 |
| | Purified water | | To 100 |
| B | Crodamol AB | Croda | 6.00 |
| | Oat Lipid Extract | Oat ® Cosmetics | 4.00 |
| | DC200 silicone fluid | Dow Corning | 1.00 |
| | Glucamate SSE20 | Lubrizol | 4.50 |
| | Glucate SS Emul | Lubrizol | 4.50 |
| | Crodacol S95 | Croda | 1.00 |
| C | Unipure Yellow LC 182 AS-EM | Sensient | 0.48 |
| | Unipure Red LC 381 AS-EM | Sensient | 0.15 |
| | Unipure Black LC 989 AS-EM | Sensient | 0.03 |
| | SunCROMA TiO2 (C47060) | Sun Chemical | 2.40 |
| D | Simulgel EG | Air Liquide | 0.60 |

2. Hand Cream

Easily absorbed hand cream which softens and nourishes dry skin for moisturised hands.

Method:
1. Add water to the main vessel.
2. Add the ingredients from Phase A to the water with stirring and heat to 70° C.
3. In a separate vessel add all ingredients from Phase B and heat to 70° C. until melted and uniform
4. Using an homogeniser, add Phase B to Phase A in the main vessel and shear for 1 minute.
6. Add Phase C to the main vessel and homogenise for a further 5 minutes until bright, shiny and uniform.
7. Commence cooling with constant stirring to ambient temperature.
8. Make to weight with purified water, record pH and viscosity.

| Phase | Common/Trade Name | Supplier | % w/w |
|---|---|---|---|
| A | Euxyl PE9010 | Schulke & Mayr | 1 |
| | Glycerin | Various | 2.5 |
| B | Crodamol GTCC | Croda | 7 |
| | Oat Lipid Extract | Oat ® Cosmetics | 5 |
| | Cutina GMS V | BASF | 3.5 |
| | Lanette O | BASF | 2.85 |
| | Stearic Acid | Various | 3.5 |
| | Shea Butter | ProTec Botanica Ltd | 1 |
| | Beeswax | ProTec Botanica Ltd | 1 |
| | Vitamin E Acetate | BASF | 0.2 |
| C | Triethanolamine 99% | BASF | 0.9 |
| | Purified Water | | To 100 |

3. Silicone Free Facial Antiageing Serum

A lightweight serum with an antioxidant complex that protects from future signs of aging, helps repair wrinkles whilst also moisturising and replenishing the skin.

Method:
1. Add water into the main vessel.
2. Using high speed mechanical stirring, add Phase A and fully disperse in water.
3. Heat Phase A to 70° C.
3. Once phase A has reached 70° C., add and disperse phase B.
4. In a separate vessel, add the ingredients from phase C and heat to 70° C. until melted
5. With both phases at 70° C., add phase C to the main vessel and homogenise for 1 minute to emulsify.
7. Add phase D and homogenise for a further 3-4 minutes until bright, shiny and uniform.
8. Transfer to a stirrer and stir cool to ambient temperature.
9. Make to weight with purified water, record pH and viscosity (adjusting pH if necessary).

| Phase | Common/Trade Name | Supplier | % w/w |
|---|---|---|---|
| | Purified Water | Various | To 100 |
| A | Disodium EDTA | Various | 0.05 |
| | Glycerin | Various | 3.00 |
| | Euxyl PE9010 | Schulke & Mayr | 1.00 |

| Phase | Common/Trade Name | Supplier | % w/w |
|---|---|---|---|
| B | Oat ® SILK 12 | Oat ® Cosmetics | 2.00 |
|   | Oat ® COM | Oat ® Cosmetics | 1.00 |
| C | Arlacel 165 | Croda | 1.50 |
|   | Oat Lipid Extract | Oat ® Cosmetics | 7.50 |
| D | Sepiplus 400 | Air Liquide | 2.00 |

4. Sun Protection Cream

Method

1. Add Purified Water into the main vessel
2. Apply high speed mechanical stirring and individually add and disperse, Disodium EDTA, Euxyl PE9010, Oat COM, Betafin and Glycerin (aqueous phase)
3. Heat this aqueous phase to 70 C
4. In a separate vessel mix Cetearyl Alcohol, Montanov 68, Caprylic/capric triglycerides, Oat Lipid Complex, Xiameter, Crodamol AB, Arlacel 165, Uvinul A Plus B, Tinosorb B (oil phase)
5. Heat and melt this oil phase at 70° C.
6. With both phases at 70° C., slowly add the oil phase to the aqueous phase and homogenise for 2-3 minutes until uniform
7. Add Sepiplus and homogenise for a further 2 minutes until smooth and uniform
8. Cool to ambient with constant mechanical stirring
9. Ensure pH is 5-6

| Trade Name/Ingredient | % w/w | Supplier |
|---|---|---|
| Disodium EDTA | 0.1 | Various |
| Euxyl PE9010 | 1 | Schulke & Mayr |
| Betafin BP20 | 1 | DuPont |
| Oat COM | 2 | Oat Cosmetics |
| Glycerin | 1 | Crestchem |
| Cetearyl Alcohol | 1.5 | Various |
| Montanov 68 | 3 | Seppic |
| Caprylic/capric triglyceride | 5 | Various |
| Oat Lipid Extract | 1 | Oat Cosmetics |
| Xiameter 200-350 cst | 2 | Various |
| Crodamol AB | 8 | Croda |
| Arlacel 165 | 1.5 | Croda |
| Uvinul A Plus B | 15 | BASF |
| Tinosorb S | 3 | BASF |
| Sepiplus 400 | 0.3 | Seppic |
| Water | 54.6 | |

5. Lip Balm

This balm softens and smooths lips.

| Phase | Ingredient name | % w/w | Supplier |
|---|---|---|---|
| A | Petroleum Jelly | 70.5 | Various |
|   | Lanolin Wax | 5 | NK Ingredients |
|   | Anhydrous Lanolin EP/ELP | 10 | NK Ingredients |
|   | Carnauba Wax | 1.5 | ProTec Botanica Ltd |
|   | Candelilla Wax | 2 | ProTec Botanica Ltd |
|   | White Beeswax | 1 | ProTec Botanica Ltd |
|   | Oat Lipid Extract | 10 | Oat Cosmetics |

Method

1. Add materials from Phase A into the main vessel.
2. Heat to 70-75° C. until melted and stir well until fully uniform.
3. Fill into containers and allow to cool.

Flavours and colours can simply be added with stirring prior to filling. 6. Hair Conditioning and Repair Mask Method 1. Add water to the main vessel.
2. Add Phase A to the water with stirring.
3. Add Phase B to the main vessel and apply homogenisation for 20 minutes until fully hydrated. Commence heating to 70° C. during this time.
4. In a separate vessel add the ingredients from Phase C and heat to 70° C. until melted and uniform
5. Add the Phase C to Phase A with homogenisation until bright and shiny
6. Add Phase D to the main vessel (as pre-made solution, adjusting levels accordingly). Cool with stirring to below 35° C.
7. Add Phase E with stirring.
8. Check pH and adjust as necessary
9. Make to weight with water and stir cool to ambient temperature.

pH: 4-5; Viscosity (sp4, 6 rpm, 30 seconds): 40,000-60,000 cps

| Phase | Ingredient name | % w/w | Supplier |
|---|---|---|---|
| A | Euxyl PE9010 | 1 | Schulke & Mayr |
| B | Natrasaol 250 HHR | 1 | ProTec Botanica Ltd |
| C | Lanette O | 5 | BASF |
|   | Oat Lipid Complex | 4 | Oat Cosmetics |
|   | Dehyquart A-CA | 0.5 | BASF |
|   | Cutina GMS V | 0.70 | BASF |
|   | Crodamol SS | 1.5 | Croda |
|   | Microcare Quat BHG | 1.0 | Thor |
| D | Potassium Hydroxide | 0.47 | Various |
| E | D-Panthenol 75W | 1 | DSM |

7. Problem Skin Balm with Oat Lipid Complex

Useful for dry skin, winter chapped skin, Ichthyosis, eczema, psoriasis, rosacea and other irritated skin problems.

| Phase | Ingredient name | % w/w | Supplier |
|---|---|---|---|
| A | Petroleum Jelly | 70.5 | Various |
|   | Carnauba Wax | 1.5 | ProTec Botanica Ltd |
|   | Candelilla Wax | 2 | ProTec Botanica Ltd |
|   | White Beeswax | 1 | ProTec Botanica Ltd |
|   | Oat Lipid Complex | 25 | Oat Cosmetics |

Method

1. Add materials from Phase A into the main vessel.
2. Heat to 70-75° C. until melted and stir well until fully uniform.
3. Fill into containers and allow to cool.
8. Pressed Powder Phase A

| Ingredient name | % w/w |
|---|---|
| Talc and methicone 1 | 61.25 |
| Nylon 12 2 | 15.00 |
| Extruded Colloidal Oatmeal | 5.00 |
| Tocopherol/glycerine-vitamin E | 1.40 |
| Iron oxide red 3 | 2.35 |
| Iron oxide yellow 3 | 2.35 |
| Iron oxide black 3 | 0.60 |
| Titanium oxide 4 | 4.00 |
| Preservative/Fragrance | q.s. |

Phase B

| Ingredient name | % w/w |
|---|---|
| BC 2161 Dimethicone and Trimethylsilyloxysilicate 5 | 4.00 |
| BC 2231 Cyclopentasiloxane and Dimethiconol 5 | 3.50 |
| Oat Lipid Complex | 0.5 |

Method

Combine phase A using a ribbon blender and micropulverise.

Combine phase B, separately, and heat the mixture to 50° C.

Spray phase B into the phase A mixture while blending.

Micropulverise until homogeneous and press at 1200-1500 PSI.

9. Loose Powder Bronzer

| Phase | Ingredient name | % w/w |
|---|---|---|
| Part 1 | Kobo Mica 1 27 | 18.15 |
| | Mica powder Y 3000 | 15 |
| | Polymethyl methacrylate BPA 500 | 5 |
| | Talc | to 100 |
| | Extruded colloidal Oatmeal | 7 |
| | Iron Oxides (C.I. 77492) (And) Isopropyl Titanium Triisostearate (And) Triethoxysilylethyl Polydimethylsiloxyethyl Dimethicone | 0.2 |
| | Iron Oxides (C.I. 77491) (And) Isopropyl Titanium Triisostearate (And) Triethoxysilylethyl Polydimethylsiloxyethyl Dimethicone | 0.1 |
| | Iron Oxides (C.I. 77499) (And) Triethoxysilylethyl Polydimethylsiloxyethyl Dimethicone (And) Isopropyl Titanium Triisostearate | 0.05 |
| | Preservatives | 0.25 |
| Part 2 | Dimethicone | 4.00 |
| | dl-alpha Tocopherol Acetate | 0.50 |
| | Oat Lipid Complex | 0.5 |
| Part 3 | Mixed colours pearls Mica (And) Iron Oxides (C.I. 77491) | 30 |
| | Mixed colours pearls Mica (And) Titanium Dioxide (And) Iron Oxides (C.I. 77491) | 3.5 |
| | Mixed colours pearls Titanium Dioxide (And) Mica (And) Iron Oxides (C.I. 77491) | 2.5 |

Method

1. Weigh and add Part 1 raw materials to the Waring Blender under a fume hood. Mix for 2-3 minutes.
2. Pre-mix Part 2.
3. Add Part 2 slowly to Part 1 under a fume hood. Mix for 2 minutes.
4. Add the Pearls and mix for 1-2 minutes.

10. Creme—Powder Blush

| Phase | Ingredient name | % w/w |
|---|---|---|
| Part 1 | SERICITE GMS-4C Mica | 17 |
| | RBTD-I2 Titanium Dioxide (And) Isopropyl Titanium Triisostearate | 10 |
| | Extruded Colloidal Oatmeal | 3 |
| | SPC/MST-547-I2 Polymethylsilsesquioxane (And) Ethylene/Methacrylate Copolymer (And) Isopropyl Titanium Triisostearate | 6 |
| | BYO-I2 Iron Oxides (C.I. 77492) (And) Isopropyl Titanium Triisostearate | 0.33 |
| | BRO-I2 Iron Oxides (C.I. 77491) (And) Isopropyl Titanium Triisostearate | 0.33 |
| | BBO-I2 Iron Oxides (C.I. 77499) (And) Isopropyl Titanium Triisostearate | 0.1 |
| | Preservatives | 0.2 |

-continued

| Phase | Ingredient name | % w/w |
|---|---|---|
| Part 2 | Wickenol 155 Ethylhexyl Palmitate | 32.55 |
| | Oat Lipid Complex | 5.0 |
| | Squalane NF Squalane | 7.00 |
| | Microcrystalline Wax SP-89 Microcrystalline Wax | 6.00 |
| | Lameform TGI Polyglycerol-3 Diisostearate | 5.50 |
| | Mineral Oil Carnation Mineral Oil | 3.00 |
| | Softisan ® 100 Hydrogenated Coco-Glycerides | 2.00 |
| | Carnauba Wax SP 63 *Copernicia Cerifera* (Carnauba) Wax | 2.00 |

Method

1. Blend Part 1 and pass through a micronizer until the colour is fully dispersed.
2. Heat Part 2 with stirring to 91-93° C. Maintain temperature for 30 minutes.
3. Add Part 1 to Part 2 and mix until homogeneous. Stir and cool to 88° C. Add Part 3.
4. Continue to mix until uniform while maintaining temperature. Fill at 85° C.

11. Non-Transfer Lipstick

| Phase | Ingredient name | % w/w |
|---|---|---|
| Part 1 | KOBOGUARD ® HRPC Hydrogenated Polycyclopentadiene (And) Polyethylene (And) *Copernicia Cerifera* (Carnauba) Wax (And) Tocopherol | 20.00 |
| | Extruded colloidal oatmeal | 5 |
| | INBP75ER Iron Oxides (C.I. 77491) (And) Isononyl Isononanoate (And) Isopropyl Myristate (And) Stearalkonium Hectorite (And) Polyhydroxystearic Acid (And) Isopropyl Titanium Triisostearate (And) Propylene Carbonate | 7.25 |
| | Candelilla Wax SP 75 *Euphorbia Cerifera* (Candelilla) Wax | 7.00 |
| | SERICITE GMS-4C Mica | 5.00 |
| | Ozokerite Wax White SP 1020P Ozokerite | 4.50 |
| | Microcrystalline Wax SP-89 Microcrystalline Wax | 2.00 |
| Part 2 | Permethyl 99AD Isododecane | 44.25 |
| | Oat Lipid Complex | 5.0 |

Method

*Use explosion-proof mixers and equipment during batching process*

1. Combine Part 1 and heat to 90° C. Mix well under propeller until colour is fully dispersed.
2. Cool to 80° C. and add Part 2.
3. Pour into moulds.

12. Sunburn Treatment

| Ingredient | % w/w |
|---|---|
| Aqua | to 100 |
| Petrolatum | 3 |
| Cetyl Alcohol | 2 |
| Dimethicone | 2 |
| Glycerin | 2 |
| Ceteath-20 | 1.7 |
| Paraffinum Liquidum | 1 |
| Oat lipid Complex | 1 |
| Sodium chloride | 0.8 |
| *Theobroma cacao* | 0.7 |
| Glyceryl stearate | 0.5 |
| Parfum | 0.3 |
| Allantoin | 0.2 |
| Hydroxyethylcellulose | 0.1 |
| Triclosan | 0.1 |
| Citric acid | 0.02 |
| Preservative | q.s |
| Extruded colloidal oatmeal | 10 |

13. Eye Cream

| Ingredient | % w/w |
|---|---|
| Aqua | to 100 |
| Butylene glycol | 6 |
| Paraffinum liquidum | 5 |
| Octyl methoxycinnamate | 4 |
| Dimethicone | 2 |
| Petrolutum | 2 |
| Cetearyl octanoate | 1.8 |
| Cetearyl alcohol | 1.6 |
| Glyceryl stearate | 1.5 |
| Cetyl alcohol | 1 |
| Oat lipid complex | 1 |
| *Prunus dulcis* | 1 |
| Glycerin | 0.57 |
| Hydrogenated vegetable glycerides citrate | 0.5 |
| Tocopheryl acetate | 0.5 |
| Bisabolol | 0.475 |
| Panthenol | 0.45 |
| Sodium phosphate | 0.42 |
| PEG-20 stearate | 0.4 |
| Isopropyl myristate | 0.2 |
| Carbomer | 0.15 |
| PEG-12 isostearate | 0.125 |
| Allantoin | 0.1 |
| Tetrasodium EDTA | 0.1 |
| Lactic acid | 0.088 |
| Disodium phophate | 0.083 |
| Potassium hydroxide | 0.051 |
| Extruded colloidal oatmeal | 4 |
| Preservative | q.s |

14. Eye Gel

| Ingredient | % w/w |
|---|---|
| Aqua | to100 |
| PVP/VA copolymer | 2 |
| Propylene glycol | 2 |
| Carbomer | 1 |
| PEG-40 hydrogenated castor oil | 1 |
| Panthenol | 1 |
| Sodium hydroxide | 0.3 |
| Phenoxyethanol | 0.2 |
| Tetrasodium EDTA | 0.1 |
| Extruded colloidal oatmeal | 0.5 |
| Oat lipid complex | 0.1 |

15. Refreshing Cream

| Ingredient | % w/w |
|---|---|
| Aqua | to 100 |
| Butylene glycol | 7.5 |
| Silica | 7.2 |
| Arabinogalactan | 5.35 |
| Dimethicone | 5.35 |
| Petrolatum | 5.35 |
| Oat lipid complex | 2 |
| Hydrated silica | 3.75 |
| Steareth-2 | 2.7 |
| *Prunus dulcis* | 2.7 |
| Steareth-21 | 0.9 |
| PVP/hexadecene copolymer | 0.8 |
| Carbomer | 0.32 |
| Sodium PCA | 0.2 |
| Parfum | 0.2 |
| Hydroxyethylcellulose | 0.16 |
| Potassium hydroxide | 0.1 |
| Propylene glycol | 0.1 |
| Extruded colloidal oatmeal | 1 |
| Preservative | q.s |

16. Night Cream

| Ingredient | % w/w |
|---|---|
| Aqua | to 100 |
| Glycerin | 5 |
| Paraffinum liquidum | 4.5 |
| Dicaprylyl maleate | 3 |
| Dimethicone | 3 |
| Petrolatum | 3 |
| Oat lipid complex | 5 |
| Paraffin | 2.9 |
| Cetyl alcohol | 2 |
| Steareth-2 | 2 |
| Glyceryl stearate | 1.5 |
| *Butyrospermum parkii* | 1.5 |
| Steareth-21 | 1 |
| Mannitol | 1 |
| Cera microcristallina | 0.262 |
| *Buxus chinensis* | 0.5 |
| Propylene glycol | 0.48 |
| Parfum | 0.4 |
| *Borago officinalis* | 0.3 |
| Hydroxyethylcellulose | 0.3 |
| Lactis proteinum | 0.3 |
| Xanthan gum | 0.25 |
| Alcohol denat. | 0.08 |
| Sodium citrate | 0.08 |
| Palmitoyl Oligopeptides | 0.75 |
| BHT | 0.05 |
| Rosemary extract | 0.04 |
| Phospholipids | 0.03 |
| Citric acid | 0.025 |
| Extruded colloidal oatmeal | 5 |
| Preservative | q.s |

17. Sun Lotion for Sensitive Skin

| Ingredient | % w/w |
|---|---|
| Aqua | to 100 |
| C12-15 alkyl benzoate | 12 |
| Butylene glycol | 5 |
| Octyl methoxycinnamate | 3.8 |
| Butyl methoxydibenzoylmethane | 3 |
| Dimethicone | 2 |
| Polyglyceryl-3 methylglucose distearate | 2 |
| Oat lipid complex | 3 |
| PVP/hexadecene copolymer | 1.75 |
| C18-36 acid glycol ester | 1.5 |
| Polysorbate 60 | 0.5 |
| Titanium dioxide | 0.3 |
| Tocopheryl acetate | 0.2 |
| Acrylates/vinyl isodecanoate crosspolymer | 0.14 |
| Potassium hydroxide | 0.035 |
| Tetrasodium EDTA | 0.02 |
| Preservative | q.s |
| Extruded colloidal oatmeal | 5 |

18. Sun Lotion for Sensitive Skin

| Ingredient | % w/w |
|---|---|
| Aqua | to 100 |
| C12-15 alkyl benzoate | 12 |
| Butylene glycol | 5 |
| Octyl methoxycinnamate | 3.8 |
| Butyl methoxydibenzoylmethane | 3 |
| Dimethicone | 2 |
| Polyglyceryl-3 methylglucose distearate | 2 |
| Oat lipid complex | 1 |
| PVP/hexadecene copolymer | 1.75 |
| C18-36 acid glycol ester | 1.5 |
| Polysorbate 60 | 0.5 |
| Titanium dioxide | 0.3 |

19. Sun Cream for Sensitive Skin

| Ingredient | % w/w |
| --- | --- |
| Tocopheryl acetate | 0.2 |
| Acrylates/vinyl isodecanoate crosspolymer | 0.14 |
| Potassium hydroxide | 0.035 |
| Tetrasodium EDTA | 0.02 |
| Preservative | q.s |
| Extruded colloidal oatmeal | 10 |

19. Sun Cream for Sensitive Skin

| Ingredient | % w/w |
| --- | --- |
| Aqua | to 100 |
| Octyl stearate | 13.5 |
| Oat lipid complex | 3 |
| Zinc oxide | 13.5 |
| Isopropyl myristate | 5 |
| Butylene glycol | 3 |
| Isohexadecane | 3 |
| Titanium dioxide | 2 |
| Methylene Bis-Benzotriazolyl Tetramethylbutylphenol | 3 |
| Polyglyceryl-3 oleate | 1.75 |
| Cetyl dimethicone copolyol | 1.35 |
| Magnesium sulfate | 0.75 |
| Sodium chloride | 0.75 |
| Aluminium stearate | 0.18 |
| Alumina | 0.15 |
| Lecithin | 0.13 |
| Isopropyl palmitate | 0.05 |
| Extruded colloidal oatmeal | 1 |

20. Sun Cream for Sensitive Skin

| Ingredient | % w/w |
| --- | --- |
| Aqua | to 100 |
| Octyl stearate | 13.5 |
| Zinc oxide | 10 |
| Isopropyl myristate | 5 |
| Butylene glycol | 3 |
| Isohexadecane | 3 |
| Titanium dioxide | 2 |
| Oat lipid complex | 5 |
| Polyglyceryl-3 oleate | 1.75 |
| Cetyl dimethicone copolyol | 1.35 |
| Magnesium sulfate | 0.75 |
| Sodium chloride | 0.75 |
| Aluminium stearate | 0.18 |
| Alumina | 0.15 |
| Lecithin | 0.13 |
| Isopropyl palmitate | 0.05 |
| Extruded colloidal oatmeal | 10 |

21. Sun Spray

| Ingredient | % w/w |
| --- | --- |
| Aqua | to 100 |
| Dicaprylyl maleate | 12 |
| Butylene glycol | 5 |
| Octyl methoxycinnamate | 4 |
| Butyl methoxydibenzoylmethane | 3.5 |
| Dimethicone | 3 |
| Oat lipid complex | 1 |
| Polyglyceryl-3 methylglucose distearate | 3 |
| Acrylates/octylacrylamide copolymer | 2 |
| C18-36 acid glycol ester | 1.5 |
| Triethanolamine | 0.5 |
| Tocopheryl acetate | 0.2 |
| Acrylates/vinyl isodecanoate copolymer | 0.05 |
| Tetrasodium EDTA | 0.02 |
| Potassium hydroxide | 0.015 |
| Preservative | q.s |
| Extruded colloidal oatmeal | 0.5 |

22. Anti-Ageing Foundation

| Ingredient | % w/w |
| --- | --- |
| Aqua | to 100 |
| Butylene glycol | 9.8 |
| Cetearyl isononanoate | 4.9 |
| Dimethicone | 3.2 |
| Glycerin | 1.96 |
| Silica | 1.9 |
| Caprylic/capric triglyceride | 1.67 |
| Paraffinum liquidum | 1.67 |
| Petrolatum | 1.67 |
| Hydrogenated coco-glycerides | 1.67 |
| Cetearyl octanoate | 1.5 |
| Cetearyl alcohol | 1.35 |
| Octyl methoxycinnamate | 1.28 |
| Talc | 1 |
| Glyceryl stearate | 0.95 |
| PEG-100 stearate | 0.9 |
| Oat lipid complex | 1 |
| Butyl methoxydibenzoylmethane | 0.6 |
| Saccharide isomerate | 0.54 |
| Lactic acid | 0.45 |
| Sodium polyacrylate | 0.45 |
| Boron nitride | 0.42 |
| Sodium PCA | 0.4 |
| Palmitoyl oligopeptides | 1 |
| *Borago officinalis* | 0.4 |
| Tocopheryl acetate | 0.4 |
| PVP/hexadecene copolymer | 0.4 |
| PEG-20 stearate | 0.33 |
| Glycolic acid | 0.2 |
| Sodium stearoyl lactylate | 0.2 |
| Isopropyl myristate | 0.17 |
| Polyaminopropyl biguanide | 0.16 |
| Tetrasodium EDTA | 0.1 |
| Xanthan gum | 0.1 |
| Citric acid | 0.06 |
| Alcohol denat. | 0.04 |
| Lecithin | 0.037 |
| Preservative | q.s |
| Extruded colloidal oatmeal | 1 |

23. Gentle Shampoo

| Ingredient | % w/w |
| --- | --- |
| Aqua | to 100 |
| Sodium laureth sulfate | 8 |
| Cocamidopropyl betaine | 3 |
| Sodium chloride | 1.8 |
| Cocamide DEA | 1.6 |
| PEG-6 cocamide | 1 |
| Parfum | 0.5 |
| Panthenol | 0.4 |
| Propylene glycol | 0.3 |
| Benzophenone-4 | 0.2 |
| Glycerin | 0.2 |
| Phenoxyethanol | 0.1 |
| Extruded colloidal oatmeal | 1 |
| Oat Protein | 0.5 |
| Oat lipid complex | 0.1 |

The invention claimed is:

1. An oat lipid extract comprised of an extract of crude oil waxy residue comprising a neutral lipid fraction and a polar lipid fraction, the neutral lipid fraction comprising at least 3% sterols, the polar lipid fraction forming at least 30% w/w of the oat lipid extract, and the extract comprising:
  a) at least 6% w/w of galactosyl acyl glycerols, including one or more of monogalacosyldiacylglycerols and diacylgalactosyldiacylglycerols;
  b) at least 9% w/w phospholipids, including one or more of phosphatidyl choline, phosphatidylethanolamine, phosphatidyl glycerol, phosphatidyl serine and/or phosphatidyl inositol; and
  c) at least 4% w/w long chain base compounds, including one or more of ceramides, glucosyl hydroxyceramides, glycosylinositophosphohydroxyceramides and/or hydroxyceramides;
  wherein the oat lipid extract contains less than 0.5% solvent and substantially free of sugars.

2. The oat lipid extract of claim 1, which contains less than 0.1% solvent.

3. The oat lipid extract of claim 1, which has been extracted from oats of the species *Avena sativa*.

4. The oat lipid extract of claim 1, wherein the polar lipid fraction forms at least 35% w/w of the oat lipid extract.

5. The oat lipid extract of claim 1, wherein the polar lipid fraction forms from about 30% w/w to about 50% w/w of the oat lipid extract.

6. The oat lipid extract of claim 1, wherein the long chain base compounds comprise compounds containing one or more of the following long chain bases: sphinganine, sphingosine, 4-hydroxysphinganine, 4-hydroxysphin-8-enine and/or 4,8-sphingadiene.

7. The oat lipid extract of claim 6, which contains ceramides, glucosyl hydroxyceramides, glycosylinositophosphohydroxyceramides and hydroxyceramides in a molar ratio of 1:2:2:1±25%.

8. The oat lipid extract of claim 7, which contains one or more of ceramide NS, ceramide NP, ceramide EOH, ceramide AS and/or ceramide AP.

9. The oat lipid extract of claim 1, wherein the sterols comprise one or more of delta-5-avenasterol, beta-sitosterol, campesterol, 24-methylene cholesterol, capestanol, stigmasterol, delta-7-campesterol, delta-5,23-stigmastadienol, clerosterol, sitostanol, delta-5,24-stigmastadienol, delta-7-stigmastenol and/or delta-7-avenasterol.

10. The oat lipid extract of claim 9, wherein the sterols comprise delta-5-avenasterol, beta-sitosterol and campesterol.

11. The oat lipid extract of claim 1, wherein the polar lipid fraction comprises phospholipids and the neutral lipid fraction comprises sterols, and the phospholipids and sterols are present in a molar ratio of 3:2±25%.

12. The oat lipid extract of claim 1 which causes up-regulation of one or more genes on topical application to the skin, wherein the one or more genes are selected from IL8, trichohyalin, repetin, occludin, and hyaluronal synthase 3.

13. A cosmetic or pharmaceutical composition comprising the oat lipid extract of claim 1.

14. A composition according to claim 13, for the treatment of dry skin, dry or chapped lips, dry hair, psoriasis, eczema, sunburn, skin redness, skin irritation, skin itchiness, dry/itchy legs, aged skin, scars, stretch marks, wounds, damaged collagen and elastin and/or ichthyosis.

15. A cosmetic composition according to claim 13, which is intended for use as an antiaging composition, a moisturising composition, a shampoo, a conditioning composition, make-up, a hydrating composition and/or a sunscreen.

16. A composition according to claim 13, wherein the composition further comprises one or more additional agents selected from: anti-acne actives, anti-bacterial agents, anti-inflammatory agents, anti-irritant agents, soothing agents, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, peptides, herbal extracts, conditioning agents, moisturising agents, emollients, astringent or antiperspirant compounds, biocidal compounds, sunscreens or UV absorbers, pigments, perfumes, anti-aging agents, enzymes, proteins, vitamins or skin care agents.

17. A composition according to claim 13, wherein the composition comprises from 0.05% to 10% w/w oat lipid extract.

18. A composition according to claim 13, wherein the composition comprises from 0.1% to 5% w/w oat lipid extract.

19. A method of manufacturing the oat lipid extract of claim 1, comprising:
  a) taking a crude oil waxy residue produced as a by-product during the multi-stage solvent fractionation of oats;
  b) carrying out solvent/water fractionation on the waste product to produce an extract;
  c) removing the solvent and water from the extract.

20. The method of claim 19, wherein the solvent is ethanol.

* * * * *